US011389401B2

(12) United States Patent
Bonelli et al.

(10) Patent No.: US 11,389,401 B2
(45) **Date of Patent: *Jul. 19, 2022**

(54) COMBINATION THERAPY FOR COPD

(71) Applicant: CHIESI FARMACEUTICI S.P.A., Parma (IT)

(72) Inventors: Sauro Bonelli, Parma (IT); Francesca Usberti, Parma (IT); Enrico Zambelli, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,427

(22) Filed: Oct. 16, 2018

(65) Prior Publication Data
US 2019/0046433 A1 Feb. 14, 2019

Related U.S. Application Data

(63) Continuation of application No. 14/812,190, filed on Jul. 29, 2015, now Pat. No. 10,159,645, which is a continuation of application No. 12/977,159, filed on Dec. 23, 2010, now abandoned.

(30) Foreign Application Priority Data

Dec. 23, 2009 (EP) .................................... 09180671

(51) Int. Cl.

| | |
|---|---|
| *A61K 9/00* | (2006.01) |
| *A61K 9/12* | (2006.01) |
| *A61K 31/16* | (2006.01) |
| *A61K 31/167* | (2006.01) |
| *A61K 31/40* | (2006.01) |
| *A61K 31/573* | (2006.01) |
| *A61K 45/06* | (2006.01) |
| *B65B 3/04* | (2006.01) |
| *B65B 7/28* | (2006.01) |
| *B65B 31/00* | (2006.01) |
| *A61P 11/00* | (2006.01) |
| *A61P 11/08* | (2006.01) |

(52) U.S. Cl.

CPC .............. *A61K 9/008* (2013.01); *A61K 9/124* (2013.01); *A61K 31/16* (2013.01); *A61K 31/167* (2013.01); *A61K 31/40* (2013.01); *A61K 31/573* (2013.01); *A61K 45/06* (2013.01); *B65B 3/04* (2013.01); *B65B 7/285* (2013.01); *B65B 31/003* (2013.01)

(58) Field of Classification Search
CPC ........ A61K 9/008; A61K 9/124; A61K 31/16; A61K 31/167; A61K 31/40; A61K 31/573; A61K 45/06; B65B 3/04; B65B 31/003; A61P 11/08; A61P 43/00; A61M 15/009

See application file for complete search history.

(56) References Cited

U.S. PATENT DOCUMENTS

| | | | | |
|---|---|---|---|---|
| 5,676,930 | A | 10/1997 | Jager et al. | |
| 6,475,467 | B1 | 11/2002 | Keller et al. | |
| 6,585,958 | B1 | 7/2003 | Keller et al. | |
| 6,716,414 | B2 | 4/2004 | Lewis et al. | |
| 8,313,732 | B2 | 11/2012 | Davies et al. | |
| 9,402,825 | B2 | 8/2016 | Pasquali et al. | |
| 9,554,992 | B2 | 1/2017 | Brambilla et al. | |
| 9,808,422 | B2 | 11/2017 | Pasquali et al. | |
| 10,159,645 | B2 * | 12/2018 | Bonelli | A61K 9/124 |
| 10,596,113 | B2 * | 3/2020 | Bonelli | A61K 31/167 |
| 10,596,149 | B2 * | 3/2020 | Bonelli | A61K 31/167 |
| 10,806,701 | B2 * | 10/2020 | Bonelli | A61K 31/573 |
| 2002/0025299 | A1 | 2/2002 | Lewis et al. | |
| 2004/0101483 | A1 | 5/2004 | Muller-Walz et al. | |
| 2005/0095206 | A1 | 5/2005 | Vega et al. | |
| 2005/0175549 | A1 * | 8/2005 | Goede | A61P 11/08 424/46 |
| 2006/0171899 | A1 | 8/2006 | Adjei et al. | |
| 2006/0257324 | A1 | 11/2006 | Lewis et al. | |
| 2007/0196285 | A1 | 8/2007 | Maus et al. | |
| 2008/0274189 | A1 * | 11/2008 | Collingwood | A61P 11/08 424/484 |
| 2009/0209502 | A1 | 8/2009 | Haeberlin et al. | |
| 2011/0132355 | A1 | 6/2011 | Gerhart et al. | |
| 2011/0146677 | A1 | 6/2011 | Bonelli et al. | |
| 2011/0150783 | A1 | 6/2011 | Bonelli et al. | |
| 2011/0150784 | A1 | 6/2011 | Bonelli et al. | |

(Continued)

FOREIGN PATENT DOCUMENTS

| | | |
|---|---|---|
| CA | 2 338 680 A1 | 2/2000 |
| EP | 1 157 689 | 11/2001 |

(Continued)

OTHER PUBLICATIONS

European Search Report in Application No. 09180671.1, dated May 12, 2010.
"Glycopyrronium Bromide" Martindale 29th Edtion p. 532-533 (1989).
Qvar-Beclomethasone Dipropionate aerosol, Patient Information, Aug. 2003.
Office Action dated Nov. 21, 2014, in corresponding Japanese Patent Application No. 2012-545323 (with English-language Translation).
Papi et al., Beclomethasone/formoterol versus budesonide/formoterol combination therapy in asthma, *Eur. Respir. J.*; 2007; 29: 682-689.

(Continued)

*Primary Examiner* — Mina Haghighatian
(74) *Attorney, Agent, or Firm* — Oblon, McClelland, Maier & Neustadt, L.L.P.

(57) ABSTRACT

Aerosol formulations comprising glycopyrronium bromide in combination with formoterol are useful for the prevention or treatment of chronic obstructive pulmonary disease. The formulation further comprises a HFA propellant, a co-solvent, and an amount of inorganic acid sufficient to stabilize both the glycopyrronium bromide and the formoterol components. Optionally the formulation may further comprise beclometasone dipropionate.

12 Claims, No Drawings

(56) References Cited

U.S. PATENT DOCUMENTS

| | | |
|---|---|---|
| 2014/0363383 A1 | 12/2014 | Bonelli et al. |
| 2014/0363384 A1 | 12/2014 | Bonelli et al. |
| 2015/0182450 A1 | 7/2015 | Bonelli et al. |
| 2015/0182459 A1 | 7/2015 | Bonelli et al. |
| 2015/0306026 A1 | 10/2015 | Bonelli et al. |
| 2016/0303044 A1 | 10/2016 | Bonelli et al. |
| 2016/0303045 A1 | 10/2016 | Bonelli et al. |
| 2017/0079949 A1 | 3/2017 | Bonelli et al. |
| 2017/0095444 A1 | 4/2017 | Bonelli et al. |
| 2018/0028439 A1 | 2/2018 | Scuri et al. |

FOREIGN PATENT DOCUMENTS

| | | |
|---|---|---|
| EP | 1 894 568 | 3/2008 |
| JP | 08-509459 | 10/1996 |
| JP | 2002-521424 | 7/2002 |
| JP | 2008-532674 | 8/2008 |
| JP | 2009-502415 | 1/2009 |
| JP | 2009-520711 | 5/2009 |
| JP | 2009-534333 | 9/2009 |
| WO | WO 94/13262 | 6/1994 |
| WO | WO 00/06121 | 2/2000 |
| WO | WO 00/07567 | 2/2000 |
| WO | WO 02/083079 | 10/2002 |
| WO | 2004/054580 | 7/2004 |
| WO | 2005/074900 | 8/2005 |
| WO | 2006/008213 | 1/2006 |
| WO | WO 2006/105401 A2 | 10/2006 |
| WO | WO 2007/071313 | 6/2007 |
| WO | WO 2007/121913 | 11/2007 |
| WO | 2008/000482 | 1/2008 |
| WO | WO 08/025787 | 3/2008 |
| WO | WO 2009/051818 | 4/2009 |

OTHER PUBLICATIONS

Jan. 16, 2015, Notice of Opposition in EP 2 515 855 (EP counterpart to U.S. Appl. No. 14/812,190).

Jul. 31, 2015, Reply filed in Opposition in EP 2 515 855 (EP counterpart to U.S. Appl. No. 14/812,190).

Jan. 29, 2016, Summons to Attend to Oral Proceedings and Preliminary Opinion of Opposition Division in Opposition in EP 2 515 855 (EP counterpart to U.S. Appl. No. 14/812,190).

"Glycopyrrodium Bromide"in Martindale: The Complete Drug Reference, vol. 33, 2002, p. 467.

"Glycoppyrolate," O'Neil, Maryadele J. The Merck Index: An Encyclopedia of Chemicals, Drugs, and Biologicals. Whitehouse Station, N.J: Merck, (2006), 4504.

Tzou et al. (1997), Journal of Pharmaceutical Sciences 86(12):1352-1357.

Sep. 9, 2016 Submission of Opponent in Opposition in EP 2 515 855 (EP counterpart to U.S. Appl. No. 14/812,190).

Bean, et al., "Kinetics and mechanisms in stability of drugs," Advances in Pharmaceutical Sciences, vol. 2, 1967, pp. 38-41.

Declaration of Enrico Zambelli captioned U.S. Appl. No. 12/977,159 and dated Aug. 20, 2014.

Oct. 6, 2016 Submission of Patent Owner in Opposition in EP 2 515 855 (EP counterpart to U.S. Appl. No. 14/812,190).

Kazempour, "The Alkaline Hydrolysis of Esters in Aqueous-Organic Solvent Mixtures," PhD thesis University of Bradford, 1978, 89-102.

Yates, Keith et al., "Mechanisms of Ester Hydrolysis in Aqueous Sulfuric Acids," Contribution from the Department of Chemistry, Nov. 3, 1966, 2686.

Carey, Francis et al., "Part A: Structure and Mechanisms," Advanced Organic Chemistry, vol. 4, 2000, 474-475.

Hopkinson, A.G., "Acid-catalysed Hydrolysis of Alkyl Benzoates" Phys. Org, Oct. 7, 1968, 203-205.

Ferreira, "Hammett Correlations and Their Applications in Elucidating Reaction Mechanism," Stolz Group Literature Seminar, Jul. 17, 2003.

Bender, Myron, "Mechanisms of Catalysis of Nucleophilic Reactions of Carboxylic Acid Derivatives," Department of Chemistry, Sep. 28, 1959, 70-71.

Physical Property Data Sheet for Zephex 134a, retrieved from http://www.mexichemfluor.com/products/medical/zephex134a/ on Sep. 23, 2016.

Oct. 7, 2016 Opponent's Letter Regarding Opposition Procedure in Opposition in EP 2 515 855 (EP counterpart to U.S. Appl. No. 14/812,190).

Francis A. Carey et.al., Advanced Organic Chemistry, Fourth Edition, Part A: Structure and Mechanisms, Chapter 8 Reactions of Carbonyl Compounds, pp. 474-479 (1937).

D. Ganderton et al., "The Formulation and Evaluation of a CFC-Free Budesonide Pressurised Metered Dose Inhaler," *Respiratory Medicine*, (2003), (Supplement D), pp. 54-59.

Robert O. Williams III, et al., "Moisture Uptake and Its Influence on Pressurized Metered-Dose Inhalers", *Pharmaceutical Development and Technology*, 5(2), 153-162 (2000).

Peter Sykes, "A Guidebook to Mechanism in Organic Chemistry," *Fellow of Christ's College*, Cambridge, Longman Group Ltd., pp. 238-244 (1961).

Jerry March, Advanced Organic Chemistry, Fourth Edition, Reactions, Mechanisms, and Structure, pp. 378-398 (1929).

Andrew Streitwieser, Jr., et al., Introduction to Organic Chemistry, Second Edition, Chapter 5, pp. 86-88 and Chapter 19, pp. 539-548 (1973).

G.F. Holland et al., "Labilization of Ester Bonds in Aminocyclitol Derivatives. I. Derivatives of *myo*- and *scyllo*-Inositols and of Streptamine,"*Myo-and Scyllo-Inositol* Derivatives, Contribution from the National Institute of Arthritis and Metabolic Diseases, National Institutes of Health, and the Naval Medical Research Institute, vol. 80 Nov. 20, 1958, pp. 6031-6035.

Thomas S. Ingallinera, et al., "Compatibility of Glycopyrrolate Injection with Commonly Used Infusion Solutions and Additives" Am. J. Hosp. Pharm. 36:508-510 Apr. 1979, with appended correction, Am. J. Hosp. Pharm. 36:745 Jun. 1979.

Acetylcholine Chloride, http://www.sigmaaldrich.com/catalog/product/sigma/a6625?lanq=en&region=GB (retrieved Feb. 23, 2017).

Ranga Narayanan, "Interfacial Processes and Molecular Aggregation of Surfactants", Advances in Polymer Science, ISSN 0065-3195, p. 60 and 68-70 (2008).

Oct. 26, 2016 Grounds for Decision in Opposition in EP 2 515 855 (EP counterpart to U.S. Appl. No. 14/812,190).

Mar. 6, 2017 Opponent's Statement of Grounds of Appeal in EP 2 515 855 with Annex (EP counterpart to U.S. Appl. No. 14/812,190).

Jorgen Vestbo, et al., "The Lancet", Trinity Manuscript Supplement, Nov. 8, 2016 (20 pages).

Jorgen Vestbo, et al., 2017, "Single inhaler extrafine triple therapy versus long-acting muscarinic antagonist therapy for chronic obstructive pulmonary disease (TRINITY): a double-blind, parallel group, randomised controlled trial," Lancet, 389(2017):1919-1929.

Dave Singh, et al., "Triple Therapy in COPD: New Evidence with the Extrafine Fixed Combination of Beclomethasone Dipropionate, Formoterol Fumarate, and Glycopyrronium Bromide," International Journal of COPD, 2017: 12 (pp. 2917-2928).

Dave Singh, et al., "Single Inhaler Triple Therapy Versus Inhaled Corticosteroid Plus Long-Acting $\beta^2$-agonist Therapy for Chronic Obstructive Pulmonary Disease (Triology): A Double-Blind, Parallel Group, Randomised Controlled Trial," Lancet, vol. 388, Sep. 3, 2016, pp. 963-973.

"Single Inhaler Triple Therapy for COPD", DTB, vol. 55. No. 12 (Dec. 2017), pp. 138-141.

Jul. 19, 2017, Submission in Opposition Proceedings in EP 2 515 855 (EP counterpart to U.S. Appl. No. No. 14/812,190).

Jul. 19, 2017, Observations of the Proprietor/Respondent in Response to the Opponent's Appeal, in Opposition in EP 2 515 855 (EP counterpart to U.S. Appl. No. 14/812,190).

Christian Reichardt, "Solvents and Solvent Effects in Organic Chemistry," Third, Updated and Enlarged Edition, (2003).

V. Rangaiah, et al., "Effect of Polarity of the Solvent on the Acid Hydrolysis of Nitrophenyl Esters," *Indian J. Chem.*,, vol. 5, Oct. 1967 (pp. 483-485).

(56) References Cited

OTHER PUBLICATIONS

B. Capon, et al., "A Comparison of Neighbouring Group Participation by Phenolic and Alcoholic Hydroxy-Groups in Ester Hydrolysis," *Chemical Communications*, (1971) pp. 389-390.
Enrico Emer, et al., "Direct Nucleophilic SN1-Type Reactions of Alcohol," *Microreview*, DOI 10.1002/ejoc.291001474.
K. Peter C. Vollhardt, et al., *Organic Chemistry Structure and Function*, Fifth Edition, (2007), pp. 334-337.
Huaping Mo, et al., "Closed-Shell Ion Paris: Cation and Aggregate Dynamics of Tetraalkylammonium Salts in an Ion-Pairing Solvent," *J. Am. Chem. Soc.*, (1997), 119, pp. 11666-11673.
Alex Avdeef, "pH-Metric log P. Part 1. Difference Plots for Determining Ion-Pair Ocanol-Water Partition Coefficients of Multiprotic Substances," *quant. Struct. Act. Relat.*, 11, 510-517 (1992).
T.S. Purewal and D.J.W. Grant, "Metered Dose Inhaler Technology", Interpharm Press Inc. US, 1998, pp. 10-17.
R.O. Williams III et al., Eds., "Advanced Drug Formulation Design to Optimize Therapeutic Outcomes", Informa Healthcare, NY, 2008, pp. 23-36.
Guidance for Industry, Nasal Spray and Inhalation Solution, Suspension, and Spray Drug Products—Chemistry, Manufacturing, and Controls Documentation, US FDA, CDER, Jul. 2002.
EPO Appeal No. T2474/11-3.3.07, Decision of Mar. 5, 2015, 21 pages, "Stable pharmaceutical solution formulations for pressurised metered dose inhalers".
Third Party Observations submitted in EP Application No. 2 515 855, on Nov. 17, 2020.
Response to Third Party Opposition in EP Application No. 10799030. 1, dated Jul. 9, 2021, with attachments D43, D44, and D45, and Auxiliary Requests AR19-AR34.

\* cited by examiner ial aerosol
COMBINATION THERAPY FOR COPD

CROSS REFERENCES TO RELATED APPLICATIONS

This application is a continuation of U.S. patent application Ser. No. 14/812,190, filed Jul. 29, 2015, now allowed; which is a continuation of U.S. patent application Ser. No. 12/977,159, filed Dec. 23, 2010, now abandoned; the disclosures of which is are incorporated herein by reference in their entireties. This application claims priority to European Patent Application No. 09180671.1, filed on Dec. 23, 2009, the disclosure of which is incorporated herein by reference in its entirety.

BACKGROUND OF THE INVENTION

Field of the Invention

The present invention relates to pharmaceutical aerosol solution formulations intended for use with pressurized metered dose inhalers. The present invention further relates to use of such formulations in the prevention and therapy of respiratory disorders, including chronic obstructive pulmonary disease (COPD).

Discussion of the Background

Glycopyrronium bromide (also known as glycopyrrolate) is a muscarinic M3 anticholinergic agent used to reduce salivation associated with administration of certain anaesthetics, and as adjunctive therapy for peptic ulcers. It has also been reported to be effective in the treatment of asthmatic symptoms (Hansel et al., *Chest,* 2005; 128:1974-1979).

WO 2005/107873 discloses the use of glycopyrrolate for the treatment of childhood asthma.

WO 01/76575 discloses a controlled release formulation for pulmonary delivery of glycopyrrolate. The formulation is intended for use in treatment of respiratory disease, in particular chronic obstructive pulmonary disease (COPD). The application focuses on dry powder formulations suitable for delivery by means of a dry powder inhaler (DPI).

WO 2005/074918 discloses combinations of glycopyrrolate with glucocorticoid drugs, and their use for treating diseases of the respiratory tract.

WO 2005/110402 discloses combinations of glycopyrrolate and a beta-2 agonist of the class of indane or of benzothiazole-2-one derivatives for treatment of inflammatory or obstructive airway diseases.

WO 2006/105401 discloses combinations of an anticholinergic, a corticosteroid and a long-acting beta-2 agonist for prevention and treatment of respiratory, inflammatory or obstructive airway diseases. The anticholinergic is optionally glycopyrrolate.

According to WO 2007/057223 and WO 2007/057222, combinations of glycopyrronium bromide respectively with an anti-inflammatory steroid and, in particular, with mometasone furoate provide a therapeutic benefit in the treatment of inflammatory and obstructive airways diseases.

WO 2007/057221 and WO 2007/057219 disclose combinations of a glycopyrronium salt with an indanyl derivative beta-2 agonist (or analogue) and respectively with an anti-inflammatory steroid and, in particular, with mometasone furoate.

Formoterol is a beta-2 agonist drug capable of relaxing smooth muscle in the bronchi and opening the airways to reduce wheezing conditions. It is commonly used in the management of asthma and other respiratory conditions.

Recently an effective combination therapy comprising formoterol fumarate and beclometasone dipropionate (a corticosteroid) has become available under the trade-name Foster®. Foster® is designed for delivery by aerosol to the lungs using a pressurized metered dose inhaler (pMDI). It has long been known that aerosol solutions of formoterol fumarate are relatively unstable and have a short shelf-life when stored under suboptimal conditions. The Foster® formulation incorporates a quantity of inorganic acid in order to stabilize the formoterol component (as described in EP 1157689).

It would be desirable to provide a clinically useful combination aerosol product that combines the therapeutic benefits of formoterol and glycopyrronium bromide, optionally in conjunction with beclometasone dipropionate. Such a product would need to be formulated in a manner such that each individual pharmaceutically active component is delivered to the lungs in effective and consistent doses over an extended product lifetime, and ideally without the need for storage under special conditions of temperature or humidity.

SUMMARY OF THE INVENTION

Accordingly, it is one object of the present invention to provide novel pharmaceutical aerosol solution formulations intended for use with pressurized metered dose inhalers.

It is another object of the present invention to provide novel methods for the prevention and therapy of respiratory disorders, including COPD.

These and other objects, which will become apparent during the following detailed description, have been achieved by the inventors' discovery that pharmaceutical aerosol formulations comprising:

(a) glycopyrronium bromide; and
(b) formoterol or a salt thereof;
dissolved in HFA propellant and a co-solvent, wherein the formulation also comprises an inorganic acid as stabilizing agent, are useful for the prevention and therapy of respiratory disorders, including COPD.

Optionally, the formulation further comprises beclometasone dipropionate.

In another aspect, the present invention provides the use of a combination product comprising glycopyrronium bromide and formoterol or a salt thereof for the prevention or treatment of COPD and other respiratory diseases.

In another aspect, the present invention provides methods for the prevention or treatment of COPD and other respiratory diseases by administering such a formulation to a subject in need thereof.

In yet another aspect, the invention provides a canister for use with a pMDI comprising:

(a) glycopyrronium bromide; and
(b) formoterol or a salt thereof;
dissolved in HFA propellant and a co-solvent, wherein the formulation also comprises an inorganic acid as stabilizing agent.

DETAILED DESCRIPTION OF THE PREFERRED EMBODIMENTS

When attempts were made to formulate a combination solution formulation product comprising both glycopyrronium bromide and formoterol it was surprisingly found that the formoterol component underwent significant degradation upon storage under conditions of high temperature and high relative humidity, to an extent that made the product clinically and commercially non-viable. This was despite the presence of acid in the formulation, which would normally be adequate to stabilise the formoterol component.

It also emerged that glycopyrronium bromide is normally unstable in aerosol solution formulations based on HFA and co-solvent, but is stabilized by the inclusion of acid in the formulation.

Upon further analysis it was shown that in the presence of glycopyrronium bromide a portion of the formoterol component undergoes degradation to a range of different products. Under suboptimal conditions the amount of the degradation product termed DP3 can exceed the identification and qualification reporting thresholds for new drug products (as defined in ICH Guideline Q3B(R2)). Thus, it became clear that the formulation needed to be altered so as to improve formoterol stability and reduce the levels of DP3 and other unwanted degradation products.

Subsequent experimentation has revealed that one successful approach to avoiding these stability issues is the inclusion of an optimised amount of acid in the formulation so that both the formoterol and the glycopyrronium bromide components are stabilized. In particular, the present inventors found that inclusion of an amount of an acid equivalent to an amount of 1M HCl in the range of 0.1 to 0.3 µg/µl, preferably 0.15 to 0.28 µg/µl, more preferably 0.18 to 026 µg/µl, even more preferably 0.19 to 0.245 µg/µl in the solution is sufficient to favor stabilisation of glycopyrronium bromide and formoterol over an extended period of non-optimal storage, thereby ensuring a consistent dose of glycopyrronium bromide and of formoterol for every actuation of the pMDI containing the solution formulation. The amount of acid included in the formulation is conveniently defined in terms of amount of added acid rather than in terms of resulting pH because the latter is poorly defined in non-aqueous systems such as propellant-based solutions.

A further significant discovery is that removal of oxygen from the canister headspace further stabilizes formoterol in combination solution formulations with glycopyrronium bromide.

Glycopyrronium bromide, chemically defined as 3-[(cyclopentylhydroxy-phenylacetyl)oxy]-1,1-dimethylpyrrolidinium bromide, has two chiral centers corresponding to four potential different stereoisomers with configurations (3R,2'R), (3S,2'R), (3R,2'S), and (3S,2'S). Glycopyrronium bromide in the form of any of these pure enantiomers or diastereomers or any combination thereof may be used in practicing the present invention. In one embodiment of the present invention the (3S,2'R), (3R,2'S)-3-[(cyclopentylhydroxyphenylacetyl)oxy]-1,1-dimethylpyrrolidinium bromide racemic mixture, also known as glycopyrrolate, is preferred. Glycopyrronium bromide is present in the formulation in an amount in the range from 0.005 to 0.14% (w/w), preferably from 0.010 to 0.13% (w/w), more preferably from 0.015 to 0.04% (w/w), wherein % (w/w) means the amount by weight of the component, expressed as percent with respect to the total weight of the composition.

Glycopyrrolate is commercially available, and can be synthesized according to the process described in U.S. Pat. No. 2,956,062 or in Franko BV and Lunsford CD, *J. Med. Pharm. Chem.*, 2(5), 523-540, 1960.

The propellant component of the composition may be any pressure-liquefied propellant and is preferably a hydrofluoroalkane (HFA) or a mixture of different HFAs, more preferably selected from the group consisting of HFA 134a (1,1,1,2-tetrafluoroethane), HFA 227 (1,1,1,2,3,3,3-heptafluoropropane), and mixtures thereof. The preferred HFA is HFA 134a. HFAs may be present in the formulation in an amount in the range from 75 to 95% (w/w), preferably from 85 to 90% (w/w), wherein % (w/w) means the amount by weight of the component, expressed as percent with respect to the total weight of the composition.

The formoterol component of the formulation can be in the form of the free base, or as a salt or a solvate. Preferably the formoterol is provided in the form of formoterol fumarate. Formoterol fumarate can, for instance, be employed in the formulation in an amount of 0.005 to 0.07% w/w, preferably 0.01 to 0.02% w/w, wherein % (w/w) means the amount by weight of the component, expressed as percent with respect to the total weight of the composition.

The co-solvent incorporated into formulations of the invention has a higher polarity than that of the propellant and may include one or more substances such as a pharmaceutically acceptable alcohol, in particular ethanol, or a polyol such as propylene glycol or polyethylene glycol.

Advantageously the co-solvent is selected from the group of lower branched or linear alkyl ($C_1$-$C_4$) alcohols such as ethanol and isopropyl alcohol. Preferably the co-solvent is ethanol.

The concentration of the co-solvent will vary depending on the final concentration of the active ingredient in the formulation and on the type of propellant. For example ethanol may be used in a concentration comprised in the range from 5 to 25% (w/w), preferably from 8 to 20% (w/w), more preferably from 10 to 15% (w/w), wherein % (w/w) means the amount by weight of the component, expressed as percent with respect to the total weight of the composition. In one of the preferred embodiments the concentration of ethanol is 12% (w/w).

The ratio of propellant to co-solvent in the formulation is in the range from 50:50 to 95:5 (w/w).

It is envisaged that HCl of different molarity or alternative inorganic acids (mineral acids) could substitute for 1M HCl in the formulations of the invention. For instance, alternative acids could be any pharmaceutically acceptable monoprotic or polyprotic acid, such as (but not limited to): hydrogen halides (hydrochloric acid, hydrobromic acid, hydroiodic acid etc.) phosphoric acid, nitric acid, sulphuric acid, and halogen oxoacids.

It is preferred that the pharmaceutically active components of the composition are substantially completely and homogeneously dissolved in the mixture of propellant and co-solvent, i.e. the composition is preferably a solution formulation.

Optionally, the solution formulation compositions may comprise other pharmaceutical excipients or additives known in the art. In particular, the compositions of the present invention may comprise one or more low volatility components. Low volatility components are useful in order to increase the mass median aerodynamic diameter (MMAD) of the aerosol particles upon actuation of the inhaler and/or to improve the solubility of the active ingredient in the propellant/co-solvent mixture.

The low volatility component, when present, has a vapor pressure at 25° C. lower than 0.1 kPa, preferably lower than 0.05 kPa. Examples of low-volatility components are esters such as isopropyl myristate, ascorbyl myristate, tocopherol esters; glycols such as propylene glycol, polyethylene glycol, glycerol; and surface active agents such as saturated organic carboxylic acids (e.g. lauric, myristic, stearic acid) or unsaturated carboxylic acids (e.g. oleic or ascorbic acid).

The amount of low volatility component may vary from 0.1 to 10% w/w, preferably from 0.5 to 5% (w/w), more preferably between 1 and 2% (w/w), wherein % (w/w)

means the amount by weight of the component, expressed as percent with respect to the total weight of the composition.

In another embodiment, an amount of water comprised between 0.005 and 0.3% (w/w), wherein % (w/w) means the amount by weight of the component, expressed as percent with respect to the total weight of the composition, may optionally be added to the formulations in order to favourably affect the solubility of the active ingredient without increasing the MMAD of the aerosol droplets upon actuation.

Advantageously, the formulations of the present invention are free of excipients (such as surfactants) other than co-solvent, propellant, and a stabilizing amount of an acid.

The pharmaceutical compositions of the present invention may further comprise other, additional pharmaceutically active agents for separate, sequential or simultaneous use. Optional additional pharmaceutically active components of the composition include any known in the art for prophylaxis or treatment of respiratory diseases and their symptoms. Examples of these active components are: beta-2 agonists such as salbutamol, fenoterol, carmoterol (TA-2005), indacaterol, milveterol, vilanterol (GSK 642444), terbultaline, salmeterol, bitolterol, and metaproterenol in form of single stereoisomers or mixtures thereof and salts thereof; corticosteroids such as beclometasone dipropionate, fluticasone propionate, butixocort, mometasone furoate, triamcinolone acetonide, budesonide and its 22R-epimer, ciclesonide, flunisolide, loteprednol, and rofleponide; other anti-muscarinic drugs such as methscopolamine, ipratropium bromide, oxitropium bromide and tiotropium bromide; phosphodiesterase IV inhibitors such as: cilomilast, roflumilast, and tetomilast.

In a preferred embodiment, compositions of the present invention comprise beclometasone dipropionate (BDP) as active agent in addition to the formoterol and glycopyrronium bromide components. In that embodiment BDP is preferably present in the formulation in an amount of 0.07 to 0.41% w/w, preferably 0.1 to 0.3% w/w, wherein % (w/w) means the amount by weight of the component, expressed as percent with respect to the total weight of the composition.

The compositions of the present invention can be inhaled from any suitable pressurized MDI device known to the skilled person. Desired doses of the individual pharmaceutically active components of the formulation are dependent on the identity of the component and the type and severity of the disease condition, but are preferably such that a therapeutic amount of the active ingredient is delivered in one or two actuations. Generally speaking, doses of active ingredient are in the range of about 0.5 to 1000 μg per actuation, e.g. about 1 to 100 μg/actuation, and sometimes about 5 to 50 μg/actuation. The skilled person in the field is familiar with how to determine the appropriate dosage for each individual pharmaceutically active ingredient.

With reference to formoterol, the preferred dosage is about 0.5 to 50 μg per actuation, preferably about 1 to 25 μg per actuation, and more preferably about 5 to 15 μg per actuation. In specific embodiments the dose of formoterol fumarate is 6 or 12 μg/actuation.

With reference to glycopyrronium bromide, the preferred dosage is about 0.5 to 100 μg per actuation, preferably about 1 to 40 μg per actuation, and more preferably about 5 to 26 μg per actuation. In one specific embodiment the dose of glycopyrronium bromide is about 25 μg/actuation.

With reference to the optional component beclometasone dipropionate, the preferred dosage is about 10 to 2000 μg per actuation, preferably about 20 to 1000 μg per actuation, and more preferably about 50-250 μg per actuation. In specific embodiments the dose of beclometasone dipropionate is about 50, 100, or 200 μg/actuation.

The pharmaceutical formulation of the present invention is filled into pMDI devices known in the art. Said devices comprise a canister fitted with a metering valve. Actuation of the metering valve allows a small portion of the spray product to be released.

Part or all of the canister may be made of a metal, for example aluminum, aluminum alloy, stainless steel or anodized aluminum. Alternatively the canister may be a plastic can or a plastic-coated glass bottle.

The metal canisters may have part or all of their internal surfaces lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene (FEP), polyether sulfone (PES) or fluorinated-ethylene-propylene polyether sulfone (FEP-PES) mixtures or combination thereof. Other suitable coatings could be polyamide, polyimide, polyamideimide, polyphenylene sulfide or their combinations.

In certain embodiments canisters having their internal surface lined with FEP-PES or Teflon may be used.

In other particular embodiments canisters made of stainless steel may be used.

The container is closed with a metering valve for delivering a daily therapeutically effective dose of the active ingredient. Generally, the metering valve assembly comprises a ferrule having an aperture formed therein, a body molding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise elastomeric material such as EPDM, chlorobutyl rubber, bromobutyl rubber, butyl rubber, or neoprene. EPDM rubbers are particularly preferred. The metering chamber, core, and core extension are manufactured using suitable materials such as stainless steel, polyesters (e.g. polybutyleneterephthalate (PBT)), or acetals. The spring is manufactured in stainless steel eventually including titanium. The ferrule may be made of a metal, for example aluminum, aluminum alloy, stainless steel or anodized aluminum. Suitable valves are available from manufacturers such as Valois, Bespak plc and 3M-Neotechnic Ltd.

The pMDI is actuated by a metering valve capable of delivering a volume of between 25 to 100 μl, preferably between 40 to 70 μl, and optionally about 50 μl, or about 63 μl per actuation.

Each filled canister is conveniently fitted into a suitable channeling device prior to use to form a metered dose inhaler for administration of the medicament into the lungs of a patient. Suitable channeling devices comprise, for example a valve actuator and a cylindrical or cone-like passage through which medicament may be delivered from the filled canister via the metering valve to the mouth of a patient e.g. a mouthpiece actuator. In a typical arrangement, the valve stem is seated in a nozzle block which has an orifice leading to an expansion chamber. The expansion chamber has an exit orifice which extends into the mouthpiece. Actuator (exit) orifices having a diameter in the range 0.15 to 0.45 mm and a length from 0.30 to 1.7 mm are generally suitable. Preferably, an orifice having a diameter from 0.2 to 0.44 mm is used, e.g. 0.22, 0.25, 0.30, 0.33, or 0.42 mm.

In certain embodiments of the present invention, it may be useful to utilize actuator orifices having a diameter ranging from 0.10 to 0.22 mm, in particular from 0.12 to 0.18 mm, such as those described in WO 03/053501. The use of said fine orifices may also increase the duration of the cloud generation and hence, may facilitate the coordination of the cloud generation with the slow inspiration of the patient.

In case the ingress of water into the formulation is to be avoided, it may be desired to overwrap the MDI product in a flexible package capable of resisting water ingress. It may also be desirable to incorporate a material within the packaging which is able to adsorb any propellant and co-solvent which may leak from the canister (e.g. a molecular sieve).

Optionally the MDI device filled with the formulation of the present invention may be utilized together with suitable auxiliary devices favoring the correct use of the inhaler. Said auxiliary devices are commercially available and, depending on their shape and size, are known as "spacers", "reservoirs" or "expansion chambers". Volumatic™ is, for instance, one of the most widely known and used reservoirs, while Aerochamber™ is one of the most widely used and known spacers. A suitable expansion chamber is reported for example in WO 01/49350.

The formulation of the present invention may also be used with common pressurized breath-activated inhalers, such as those known with the registered names of Easi-Breathe™ and Autohaler™.

The efficacy of an MDI device is a function of the dose deposited at the appropriate site in the lungs. Deposition is affected by the aerodynamic particle size distribution of the formulation which may be characterised in vitro through several parameters.

The aerodynamic particle size distribution of the formulation of the present invention may be characterized using a Cascade Impactor according to the procedure described in the European Pharmacopoeia $6^{th}$ edition, 2009 (6.5), part 2.09.18. An Apparatus E, operating at a flow rate range of 30 l/minute to 100 l/minute or an Apparatus D—Andersen Cascade Impactor (ACI)—, operating at a flow rate of 28.3 l/minute, Deposition of the drug on each ACI plate is determined by high performance liquid chromatography (HPLC).

The following parameters of the particles emitted by a pressurized MDI may be determined:

i) mass median aerodynamic diameter (MMAD) is the diameter around which the mass aerodynamic diameters of the emitted particles are distributed equally;
ii) delivered dose is calculated from the cumulative deposition in the ACI, divided by the number of actuations per experiment;
iii) respirable dose (fine particle dose=FPD) is obtained from the deposition from Stages 3 (S3) to filter (AF) of the ACI, corresponding to particles of diameter≤4.7 microns, divided by the number of actuations per experiment;
iv) respirable fraction (fine particle fraction=FPF) which is the percent ratio between the respirable dose and the delivered dose; and
v) "superfine" dose is obtained from the deposition from Stages 6 (S6) to filter, corresponding to particles of diameter≤1.1 microns, divided by the number of actuations per experiment.

The solutions of the present invention are capable of providing, upon actuation of the pMDI device in which they are contained, a total FPF higher than 40%, preferably higher than 50%, more preferably higher than 60%.

Moreover, the formulations of the present invention are capable of providing, upon actuation, a fraction higher than or equal to 30% of emitted particles of diameter equal to or less than 1.1 microns as defined by the content stages S6-AF of an Andersen Cascade Impactor, relative to the total fine particle dose collected in the stages S3-AF of the impactor. Preferably, the fraction of emitted particles of diameter equal to or less than 1.1 microns is higher than or equal to 40%, more preferably higher than 50%, even more preferably higher than 60%, most preferably higher than 70%.

According to a further aspect of the present invention there is provided a method of filling an aerosol inhaler with a composition of the present invention. Conventional bulk manufacturing methods and machinery well known to those skilled in the art of pharmaceutical aerosol manufacture may be employed for the preparation of large-scale batches for the commercial production of filled canisters.

A first method comprises:

a) preparing a solution of glycopyrronium bromide and formoterol fumarate and optionally beclometasone dipropionate in an optional co-solvent (e.g. ethanol), mineral acid, propellant comprising a HFA and optionally a low volatility component at a temperature from −50 to −60° C. at which the formulation does not vaporize;
b) cold-filling the inhaler with the prepared solution; and
c) placing the valve onto the empty can and crimping.

An alternative method comprises:

a) preparing a solution of glycopyrronium bromide and formoterol fumarate and optionally beclometasone dipropionate in a co-solvent (e.g. ethanol), mineral acid, and optionally a low volatility component;
b) filling the open can with the bulk solution;
c) placing the valve onto the can and crimping; and
d) pressure-filling the can with the HFA propellant through the valve.

A further alternative method comprises:

a) preparing a solution of glycopyrronium bromide, formoterol fumarate (and optionally beclometasone dipropionate) and mineral acid in optional co-solvent (e.g. ethanol), optional low volatility component and HFA propellant using a pressurised vessel;
b) placing the valve onto the empty can and crimping; and
c) pressure-filling the can with the final solution formulation through the valve.

In one embodiment of the present invention, oxygen is substantially removed from the headspace of the aerosol canister using conventional techniques in order to further stabilize the formoterol component, especially at higher acid concentrations. This can be achieved in different ways depending on the method of filling the container. Purging can be achieved by vacuum crimping or by using propellant, for instance. In a preferred embodiment, the second filling method described above is modified to incorporate an oxygen purge into step (c) by vacuum crimping.

The packaged formulations of the present invention are stable for extended periods of time when stored under normal conditions of temperature and humidity. In a preferred embodiment, the packaged formulations are stable for at least 6 months at 25° C. and 60% RH, more preferably for at least 1 year, most preferably for at least 2 years. Stability is assessed by measuring content of residual active ingredient. A "stable" formulation as defined herein means one retaining at least about 85%, preferably at least about 90%, and most preferably at least about 95% of residual content of each active ingredient at a given time point, as measured by HPLC-UV VIS.

The optimized stable formulations meet the specifications required by the ICH Guideline Q1B or CPMP/QWP/122/02 Rev.1 relevant for drug product stability testing for the purposes of drug registration.

The combination product compositions of the present invention may be used for prophylactic purposes or therapeutic purposes or for symptomatic relief of a wide range of conditions, and in one aspect the invention therefore relates to use of any of these pharmaceutical compositions as a medicament. In particular, the combination products of the present invention are useful in the prevention or treatment of many respiratory disorders, such as asthma of all types and chronic obstructive pulmonary disease (COPD).

Thus, in another aspect the present invention relates to a method of preventing or treating a respiratory disease, such as COPD, comprising administering to a patient in need of such treatment a therapeutically effective amount of a pharmaceutical composition according to the present invention.

The present invention also provides the use of the pharmaceutical compositions of the present invention for the therapeutic or palliative treatment or prevention of respiratory diseases and their symptoms.

Respiratory disorders for which use of the pharmaceutical compositions of the present invention may also be beneficial are those characterized by obstruction of the peripheral airways as a result of inflammation and presence of mucus, such as chronic obstructive bronchiolitis, chronic bronchitis, emphysema, acute lung injury (ALI), cystic fibrosis, rhinitis, and adult or acute respiratory distress syndrome (ARDS).

Other features of the invention will become apparent in the course of the following descriptions of exemplary embodiments which are given for illustration of the invention and are not intended to be limiting thereof.

EXAMPLES

Example 1

A. Stability of Single, Double, and Triple Combination Aerosol Solution Formulations.

A study was performed to investigate the stability of a triple combination of formoterol fumarate (FF), glycopyrronium bromide (GLY), and beclometasone dipropionate (BDP) in an aerosol solution formulation, in canister packaging under varied storage conditions:

In addition to the triple combination, the double combinations (FF+BDP; FF+GLY) and the single agent (GLY) were included in the study to evaluate whether any potential interactions between the active ingredients could affect drug stability. GLY as single agent was formulated with and without 1M HCl to evaluate the stabilizing effect of the acid. The batch compositions are summarized in Table 1:

TABLE 1

| Batch description | Theoretical unit formulation (µg/actuation for a 63 µl valve) | | | | | | |
|---|---|---|---|---|---|---|---|
| | BDP | FF | GLY | Anhydrous ethanol | 1M HCl | HFA 134a | Total |
| FF + GLY | — | 6 | 25 | 8856 | 14 | 64899 | 73800 |
| FF + GLY + BDP | 100 | 6 | 25 | 8856 | 14 | 64799 | 73800 |
| GLY | — | — | 25 | 8856 | — | 64919 | 73800 |
| GLY + acid | — | — | 25 | 8856 | 14 | 64905 | 73800 |
| FF + BDP | 100 | 6 | — | 8856 | 14 | 64824 | 73800 |

Sample batches were stored in an inverted orientation under the following conditions and two canisters were analyzed for content at each checkpoint (after 1, 2, and 3 months of storage):
+5° C.;
+25° C./60% relative humidity (accelerated storage conditions);
+30° C./75% relative humidity; and
+40° C./75% relative humidity.

The residual content of active ingredient was measured using standard chromatographic protocols.

Results.

TABLE 2

| Batch | Beclometasone dipropionate | | | Formoterol fumarate | | | Glycopyrronium bromide | | |
|---|---|---|---|---|---|---|---|---|---|
| | 1 m | 2 m | 3 m | 1 m | 2 m | 3 m | 1 m | 2 m | 3 m |
| 5° C. | 98.8 ± 0.0 | 98.6 ± 0.4 | 96.6 ± 1.6 | 96.7 ± 1.1 | 94.6 ± 1.6 | 102.9 ± 1.6 | 98.0 ± 0.2 | 96.7 ± 1.0 | 98.8 ± 0.3 |
| 25° C./60% RH | 96.3 ± 0.8 | n.a. | 96.6 ± 0.8 | 98.1 ± 2.1 | 95.9 ± 1.0 | 96.4 ± 0.1 | 96.8 ± 0.8 | 97.5 ± 0.1 | 98.2 ± 0.1 |
| 30° C./75% RH | 96.7 ± 0.0 | 97.4 ± 1.3 | 97.1 ± 0.0 | 96.5 ± 0.6 | 97.8 ± 0.6 | 92.5 ± 0.0 | 98.2 ± 0.7 | 97.1 ± 0.5 | 98.2 ± 0.0 |
| 40° C./75% RH | 97.4 ± 0.4 | 93.3 ± 2.9 | 97.1 ± 0.8 | 95.7 ± 0.8 | 94.2 ± 2.9 | 88.6 ± 0.4 | 97.6 ± 0.0 | 97.5 ± 0.6 | 98.9 ± 0.8 |

Regarding the triple combination, BDP and GLY can contents were not significantly affected by time and temperature. In contrast, formoterol fumarate can content was highly dependent on storage conditions: the % residue with respect to time zero decreases with time and temperature. After 3 months at +30° C./75% RH, the % residue had reached 92.5%; after 3 months at +40° C./75% RH, it had decreased to 88.6%. With regard to the double combination of FF+GLY, see Table 3:

TABLE 3

| Batch | Formoterol fumarate | | | Glycopyrronium bromide | | |
|---|---|---|---|---|---|---|
| | 1 m | 2 m | 3 m | 1 m | 2 m | 3 m |
| 5° C. | 96.4 ± 0.1 | 94.6 ± 0.1 | 100.0 ± 1.1 | 97.4 ± 1.4 | 97.7 ± 1.6 | 99.0 ± 1.2 |
| 25° C./60% RH | 96.6 ± 1.2 | 95.6 ± 1.5 | 96.8 ± 0.5 | 99.2 ± 1.2 | 98.2 ± 0.1 | 98.8 ± 1.4 |
| 30° C./75% RH | 95.9 ± 0.6 | 94.0 ± 1.8 | 91.2 ± 0.4 | 98.3 ± 1.4 | 95.7 ± 1.1 | 98.1 ± 0.4 |
| 40° C./75% RH | 93.7 ± 1.5 | 90.9 ± 0.6 | 88.1 ± 0.5 | 97.5 ± 0.2 | 96.9 ± 1.0 | 98.2 ± 0.1 |

The GLY component remained stable under all of the tested conditions. As in the triple combination, the formoterol fumarate can content was strongly dependent on time and temperature: after 3 months at +30° C./75% RH, it had dropped to 91.5%; after 3 months at +40° C./75% RH, it had decreased to 88.1%. In contrast, the formoterol content in the FF+BDP double combination did not decrease rapidly over time under any of the different storage conditions. These contrasting observations lead to the conclusion that the presence of GLY in combination with formoterol fumarate has the effect of destabilizing the formoterol fumarate. The single agent formulation containing GLY was found to maintain a constant content in the presence of 1M HCl, but to be highly dependent on time and temperature of storage if the acid was omitted.

B. Analysis of Impurities/Degradation Products.

All of the formulations stored at 40° C./75% RH were tested by a standard HPLC/UV VIS method for non-chiral impurities and degradation products of the active components. An MS detector was used to confirm the molecular weights of the detected impurities/degradation products found in the FF+BDP and FF+GLY+BDP cans.

Results.

Analyzed by the HPLC/UV method, those formulations comprising both FF and GLY had high levels of degradation products related to formoterol fumarate. It was also observed that the amount of each degradation product increased with temperature. Three major degradation products were identified: DP1, DP2, and an unknown degradation product (termed DP3). Two of these degradation products (DP1, DP2) had previously been found to be present in Foster®-like formulations containing only low levels of acid.

C. Titration of Acid Content.

Since the stability and impurity test results pointed to the importance of acid in the formulations to stabilize formoterol fumarate in the presence of glycopyrronium bromide, a series of triple combination formulations was prepared with added 1M HCl varying between 0.191 µg/µl and 0.254 µg/µl. In each test pair of samples, one can had its oxygen removed by vacuum crimping in order to investigate the impact of oxygen on the degradation process. After 3 months at 25° C./60% RH, the samples were analyzed for residual can content of active ingredients and major impurities/degradation products. The GLY and BDP components were stable over the 3 months period and experienced little degradation. The results for the formoterol fumarate component are shown in Table 4.

TABLE 4

| Oxygen Removal | 1M HCl µg/µl | Formoterol fumarate (% residue vs t 0) | Sum total of degradation products (% total composition) | DP3 (% total composition) |
| --- | --- | --- | --- | --- |
| No  | 0.191 | 101.9 | 1.6 | |
| Yes | 0.191 | 104.8 | 1.7 | |
| No  | 0.211 | 99.6  | 1.4 | 0.41 |
| Yes | 0.211 | 99.8  | 1.2 | |
| No  | 0.222 | 98.5  | 1.4 | 0.59 |
| Yes | 0.222 | 99.7  | 0.91 | |
| No  | 0.234 | 92.2  | 7.8 | 6.4 |
| Yes | 0.234 | 101.3 | 0.9 | 0.26 |

Comparing those samples from which oxygen had been removed, a consistent reduction in the % of FF degradation products is observed as the acid content is raised from 0.191 µg/µl through to 0.222 and 0.234 µg/µl. The total and individual % degradation products at these acid values are far less than 1% in each case and therefore well below the identification/qualification levels for drug registration. These results also suggest that in the absence of oxygen purging an acid concentration in excess of about 0.22 µg/µl is actually counterproductive in stabilizing FF.

In summary, based on current results, a double or triple combination product comprising glycopyrronium bromide and formoterol fumarate (and optionally beclometasone dipropionate) could be optimally stabilized for clinical and commercial purposes by inclusion of 1M HCl in an amount of between 0.191 and 0.234 µg/µl, preferably between 0.19 and 0.23 µg/µl, in a solution formulation that has been purged of oxygen.

Example 2. Stability of the Triple Combination Aerosol Solution Formulations

A study was performed to investigate the stability of a triple combination of formoterol fumarate (FF), glycopyrronium bromide (GLY), and beclometasone dipropionate (BDP) in an aerosol solution formulation with different levels of 1M HCl to evaluate the stabilizing effect of the acid, in conventional aluminium canisters, provided with standard EPDM valves crimped under varied conditions (i.e. with or without oxygen removal by vacuum crimping). The batch compositions are summarized in Table 5:

TABLE 5

Theoretical unit formulation (µg/actuation for a 63 µl valve)

| Formul. N. | BDP | FF | GLY | Anhydrous ethanol | 1M HCl (conc. µg/µl) | HFA 134a | Total |
| --- | --- | --- | --- | --- | --- | --- | --- |
| 1 | 100 | 6 | 25 | 8856 | 3.1 (0.0496) | 64810 | 73800 |
| 2 | 100 | 6 | 25 | 8856 | 6.2 (0.0992) | 64807 | 73800 |
| 3 | 100 | 6 | 25 | 8856 | 8.7 (0.139) | 64805 | 73800 |
| 4 | 100 | 6 | 25 | 8856 | 12 (0.188) | 64801 | 73800 |
| 5 | 100 | 6 | 25 | 8856 | 12.5 (0.198) | 64801 | 73800 |
| 6 | 100 | 6 | 25 | 8856 | 14 (0.222) | 64799 | 73800 |
| 7 | 100 | 6 | 25 | 8856 | 14.5 (0.230) | 64799 | 73800 |
| 8 | 100 | 6 | 25 | 8856 | 15.3 (0.243) | 64798 | 73800 |
| 9 | 100 | 6 | 25 | 8856 | 16.5 (0.263) | 64797 | 73800 |

Sample batches were stored at +25° C./60% relative humidity (accelerated storage conditions) in an inverted orientation and two canisters were analysed for content at each checkpoint (after 1, 2, and 3 months of storage). The residual content of each active ingredient was measured using standard chromatographic protocols. The results after 3 months storing are reported in the following Table 6 wherein, for each formulation, beside each reference number, the code V for vacuum crimping and N for normal crimping (without oxygen removal) have been inserted.

TABLE 6

Result of the stability testing for the formulations of Table 5.

| Formulation number/ Crimping | BDP (% residue vs t 0) | FF (% residue vs t 0) | GLY (% residue vs t 0) | Impurities/Degrad. Products (% on total composition) |
|---|---|---|---|---|
| 1 N | 101.2 | 89.4 | 98.5 | 3.5 |
| 2 N | 99.6 | 89.0 | 97.5 | 2.5 |
| 3 N | 98.8 | 89.3 | 96.7 | 1.9 |
| 4 N | 100.8 | 92.5 | 98.9 | 1.7 |
| 5 N | 100.8 | 101.9 | 99.3 | 1.6 |
| 6 N | 99.8 | 99.6 | 96.8 | 1.4 |
| 7 N | 101.0 | 98.5 | 98.6 | 1.4. |
| 8 N | 100.5 | 92.2 | 97.7 | 7.8 (DP3 6.62%) |
| 5 V | 102.1 | 104.8 | 100.6 | 1.7 |
| 6 V | 101.8 | 99.8 | 98.2 | 1.2 |
| 7 V | 102.7 | 99.7 | 98.7 | 0.9 |
| 8 V | 104.6 | 101.3 | 100.2 | 1.0 |
| 9 V | 98.9 | 82.3 | 97.1 | 10.4 (DP3 > 6%) |

The experiment showed that concentrations of 1M HCl higher than 0.230 increase the formation of degradation products and in particular of DP3 in normal crimped formulations. Vacuum crimping avoids formation of the degradation products, and in particular DP3, up to 1M HCl concentration of 0.243.

In summary, the current results confirm that a triple combination product comprising glycopyrronium bromide, formoterol fumarate and, optionally, beclometasone dipropionate could be optimally stabilized for clinical and commercial purposes by inclusion of 1M HCl in an amount of between 0.19 and 0.243 µg/µl, preferably between 0.19 and 0.230 µg/µl, in a solution formulation crimped without oxygen removal and between 0.19 and 0.243 when crimped with oxygen removal.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pressurized metered dose inhaler comprising a pharmaceutical aerosol solution composition, comprising:
   (a) glycopyrronium bromide in an amount sufficient to deliver 5 to 26 µg per actuation; and
   (b) formoterol fumarate in an amount sufficient to deliver 5 to 15 µg per actuation;
   dissolved in an HFA propellant and ethanol, wherein:
   said composition comprises an acid in an amount equivalent to 0.19 to 0.245 µg/µl of 1M HCl;
   said composition comprises ethanol in an amount of 5 to 25% w/w of the total composition; and
   said composition is free of excipients other than said HFA, ethanol, and HCl.

2. A pressurized metered dose inhaler according to claim 1, wherein said pharmaceutical aerosol solution composition further comprises one or more pharmaceutically active ingredients selected from the group consisting of a corticosteroid and a phosphodiesterase (IV) inhibitor.

3. A pressurized metered dose inhaler according to claim 1, wherein said pharmaceutical aerosol solution composition further comprises beclometasone dipropionate in an amount sufficient to deliver 50 to 250 µg per actuation.

4. A pressurized metered dose inhaler according to claim 1, wherein said pharmaceutical aerosol solution composition comprises glycopyrronium bromide in an amount in the range from 0.005 to 0.14% (w/w) of the composition.

5. A pressurized metered dose inhaler according to claim 1, wherein said pharmaceutical aerosol solution composition comprises formoterol fumarate in an amount in the range from 0.005 to 0.07% (w/w) of the composition.

6. An aerosol canister, comprising a pharmaceutical aerosol solution composition comprising:
   (a) glycopyrronium bromide in an amount sufficient to deliver 5 to 26 µg per actuation; and
   (b) formoterol fumarate in an amount sufficient to deliver 5 to 15 µg per actuation;
   dissolved in an HFA propellant and ethanol, wherein:
   said composition comprises an acid in an amount equivalent to 0.19 to 0.245 µg/µl of 1M HCl;
   said composition comprises ethanol in an amount of 5 to 25% w/w of the total composition; and
   said composition is free of excipients other than said HFA, ethanol, and HCl.

7. A kit-of-parts, comprising a pharmaceutical aerosol solution composition comprising:
   (a) glycopyrronium bromide in an amount sufficient to deliver 5 to 26 µg per actuation; and
   (b) formoterol fumarate in an amount sufficient to deliver 5 to 15 µg per actuation;
   dissolved in an HFA propellant and ethanol, wherein:
   said composition comprises an acid in an amount equivalent to 0.19 to 0.245 µg/µl of 1M HCl;
   said composition comprises ethanol in an amount of 5 to 25% w/w of the total composition; and
   said composition is free of excipients other than said HFA, ethanol, and HCl,
   and further comprising one or more pharmaceutically active ingredients for separate, sequential or simultaneous administration, wherein said pharmaceutically active ingredients are selected from the group consisting of a corticosteroid and a phosphodiesterase (IV) inhibitors.

8. A pressurized metered dose inhaler according to claim 1, wherein said pharmaceutical aerosol solution composition further comprises beclometasone dipropionate in an amount in the range from 0.07 to 0.41% (w/w) of the composition.

9. A pressurized metered dose inhaler according to claim 1, in which an aerosol canister is fitted into a channelling device.

10. A pressurized metered dose inhaler according to claim 9, wherein said channelling device comprises a valve actuator and a cylindrical or cone-like passage through which said pharmaceutical aerosol solution composition may be delivered from the filled canister via the metering valve to the mouth of a patient.

11. An aerosol canister according to claim 6, which has part or all of its internal surface lined with an inert organic coating.

12. An aerosol canister according to claim 11, wherein said inert organic coating is selected from the group consisting of an epoxy-phenol resin, a perfluorinated polymer, a polyether sulfone, a fluorinated-ethylene-propylene polyether sulfone, a polyamide, a polyimide, a polyamide-imide, a polyphenylene sulphide, and mixtures thereof.

* * * * *